(12) United States Patent
Yadav et al.

(10) Patent No.: US 10,159,657 B2
(45) Date of Patent: *Dec. 25, 2018

(54) NOREPINEPHRINE COMPOSITIONS AND METHODS THEREFOR

(71) Applicant: Nevakar, Inc., Bridgewater, NJ (US)

(72) Inventors: Vivek Yadav, Henderson, NV (US); Sriramya Garapati, North Brunswick, NJ (US); Tushar Hingorani, Bridegwater, NJ (US); Iouri V. Ilitchev, Hillsborough, NJ (US); Prem Sagar Akasapu, Edison, NJ (US); Kumaresh Soppimath, Skillman, NJ (US); Navneet Puri, Lebanon, NJ (US)

(73) Assignee: NEVAKAR INC., Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/949,736

(22) Filed: Apr. 10, 2018

(65) Prior Publication Data

US 2018/0243243 A1 Aug. 30, 2018

Related U.S. Application Data

(62) Division of application No. 15/883,798, filed on Jan. 30, 2018.

(60) Provisional application No. 62/452,220, filed on Jan. 30, 2017.

(51) Int. Cl.
| | |
|---|---|
| *A61K 31/137* | (2006.01) |
| *A61P 9/02* | (2006.01) |
| *A61K 47/12* | (2006.01) |
| *A61K 47/18* | (2017.01) |
| *A61K 9/00* | (2006.01) |

(52) U.S. Cl.
CPC .......... *A61K 31/137* (2013.01); *A61K 9/0019* (2013.01); *A61K 47/12* (2013.01); *A61K 47/183* (2013.01); *A61P 9/02* (2018.01)

(58) Field of Classification Search
CPC .... A61K 31/137; A61K 9/0019; A61K 47/12; A61K 47/183
See application file for complete search history.

(56) References Cited

U.S. PATENT DOCUMENTS

| | | | |
|---|---|---|---|
| 7,199,269 B2 | 4/2007 | Dinnequin | |
| 9,433,589 B2 | 9/2016 | Hansen et al. | |
| 2004/0054012 A1 | 3/2004 | Dietlin et al. | |
| 2005/0070613 A1 | 3/2005 | Dinnequin | |
| 2008/0269347 A1 | 10/2008 | Bruss et al. | |
| 2011/0003015 A1 | 1/2011 | Baillie et al. | |
| 2012/0029085 A1 | 2/2012 | MacKay | |
| 2012/0129944 A1* | 5/2012 | Baillie | A61K 9/0019 514/653 |
| 2013/0123298 A1 | 5/2013 | Julia | |
| 2014/0308405 A1 | 10/2014 | Okada et al. | |
| 2016/0058715 A1* | 3/2016 | Rakesh | A61K 31/137 514/653 |

FOREIGN PATENT DOCUMENTS

| | | |
|---|---|---|
| CN | 102335123 A | 2/2012 |
| WO | 9413274 A1 | 6/1994 |
| WO | 2014202088 A1 | 12/2014 |
| WO | 2015128418 | 9/2015 |

OTHER PUBLICATIONS

Tremblay et al., "Stability of norepinephrine infusions prepared in dextrose and normal saline solutions," Can. J. Anesth, 2008; 55(3):163-167.
Walker et al., "Stability of Norepinephrine Solutions in Normal Saline and 5% Destrose in Water," Can J. Hosp Pharm, 2010; 63(2):113-118.
International Search Report and Written Opinion No. PCT /US2018/015779, dated May 25, 2018; 15 pgs.
Noradrenaline Data Sheet by Medsafe.gov.nz (www.medsafe.govt.nz/profs/Datasheet/n/noradrenalineinf.pdf). Date is Oct. 2010. Author name(s) unknown.

* cited by examiner

*Primary Examiner* — Theodore R. West

(57) ABSTRACT

The inventive subject matter is directed to compositions and methods for ready-to-inject norepinephrine compositions with improved stability. Most preferably, compositions presented herein are substantially antioxidant free and exhibit less than 10% isomerization of R-nor epinephrine and exhibit less than 5% degradation of total norepinephrine.

19 Claims, No Drawings

NOREPINEPHRINE COMPOSITIONS AND METHODS THEREFOR

This application is a divisional application of our copending US provisional application with Ser. No. 15/883,798, which was filed Jan. 30, 2018, which claims priority to US provisional application with Ser. No. 62/452,220, which was filed Jan. 30, 2017.

FIELD OF THE INVENTION

The field of the invention is pharmaceutical compositions comprising norepinephrine, especially as it relates to storage stable, ready-to-inject, antioxidant free compositions, and method of manufacturing such compositions.

BACKGROUND

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Norepinephrine is often used during CPR (cardio-pulmonary resuscitation), and in the treatment of cardiac arrest and profound hypotension. Norepinephrine is also used for blood pressure control in certain acute hypotensive states, including for example sympathectomy, poliomyelitis, pheochromocytomectomy, spinal anesthesia, myocardial infarction, blood transfusion, and septicemia.

Currently, norepinephrine is marketed as Levophed®, which is a concentrated 4 mg per 4 mL norepinephrine bitartrate formulation to be administered by intravenous infusion following dilution with dextrose or dextrose and sodium chloride injection. Norepinephrine is also marketed by Baxter which supplies as a norepinephrine concentrate that is free of sodium metabisulfite and packaged under nitrogen. Unfortunately, most, if not all diluted commercially available norepinephrine formulations lack storage and should therefore be discarded within one day after reconstitution when stored at room temperature. Consequently, risk for microbial contamination and dilution errors is present. In addition, Levophed also contains sodium metabisulphite as an antioxidant, and carries a warning label that sulfite may cause allergic type reactions including anaphylactic shock and life threating or less severe asthmatic episodes in susceptible people. Table 1 depicts ingredients of currently marketed norepinephrine compositions.

TABLE 1

| Composition of currently marketed Norepinephrine Bitartrate Products. | | |
|---|---|---|
| Ingredient | Levophed ® (Hospira) | Norepinephrine Bitartarate (Baxter) |
| Norepinephrine Bitartrate equivalent to Norepinephrine Base | 1 mg/mL | 1 mg/mL |
| Sodium Chloride | Isotonic | Isotonic |
| Sodium Metabisulphite | 0.2 mg/mL | — |
| pH | 3-4.5 | 3-4.5 |
| Water for injection | q.s. 1 mL | q.s 1 mL |

Stability of Levophed® and Norepinephrine bitartrate injection (Baxter), in normal saline solutions is presented in Table 2 and Table 3 where norepinephrine was diluted to a concentration of 16 μg/ml. Stability was assessed in 250 ml saline at accelerated (i.e., 40±2° C. and 75±5% relative humidity, duration as indicated) and long term stability (i.e., 25±2° C. and 60±5% relative humidity, duration as indicated) storage conditions.

TABLE 2

Stability study of Levophed ® diluted in 0.9% Saline (Hospira) at 16 μg/mL.

| | Storage Condition | | | | | | | |
|---|---|---|---|---|---|---|---|---|
| | 25 ± 2° C./60 ± 5% RH | | | | 40 ± 2° C./75 ± 5% RH | | | |
| | Time Point | | | | | | | |
| | Initial | 1 Month | 2 Month | 3 Month | Initial | 1 Month | 2 Month | 3 Month |
| Assay | 97.3 | 98.9 | 97.9 | 91.9 | 98.8 | 96.5 | 80.2 | 71.9 |
| Total Impurities | 0.05 | — | 0.71 | 8.08 | 0.03 | 1.96 | 5.29 | 9.73 |

TABLE 3

Stability study of Norepinephrine bitartrate injection [Baxter] diluted in 0.9% Saline (Hospira) at 16 µg/mL.

| | Storage Condition | | | | | | | |
|---|---|---|---|---|---|---|---|---|
| | 25 ± 2° C./60 ± 5% RH | | | | 40 ± 2° C./75 ± 5% RH | | | |
| | Time Point | | | | | | | |
| | Initial | 1 Month | 2 Month | 3 Month | Initial | 1 Month | 2 Month | 3 Month |
| Assay | 99.9 | 99.7 | 97.0 | 92.2 | 99.4 | 91.5 | 82.9 | 77.6 |
| Total Impurities | 0.08 | 1.73 | 2.68 | 10.17 | 0.10 | 2.34 | 4.46 | 6.71 |

As can be seen from the results, the norepinephrine at ready-to-inject concentrations underwent significant degradation. Oxidative degradation could possibly be reduced or even prevented by addition of effective amounts of sodium metabisulphite to the ready-to-inject norepinephrine solution. However, the quantities of sodium metabisulphite that would be administered by injection of 250 ml of the ready-to-inject solution would be substantial and detrimental to the patient. To avoid issues associated with sodium metabisulphite, efforts have been made to provide norepinephrine formulations with a non-sulfite anti-oxidant. For example US 2016/0058715 teaches a ready-to-inject dosage form of norepinephrine that uses butylated hydroxyl anisole as an anti-oxidant. While generally deemed safe for topical and cosmetic use, butylated hydroxyl anisole was shown to produce some renal and hepatic damage (e.g., *Int J Toxicol.* 2002; 21 Suppl 2:19-94).

In other attempts to provide ready-to-administer norepinephrine formulations with increased storage stability and reduced risk of human error, the pH on the injectable solution was reduced to between 3.2 and 3.6 with 40-200 µg/ml norepinephrine as is described in WO 2015/128418. While such formulations exhibited reduced degradation as compared to higher pH formulations, significant discomfort can occur at the injection site. Worse yet, at the pH used, norepinephrine isomerized relatively quickly from the active R (−) isomer to the inactive S (+) isomer. Isomerization is also encountered at exposure of norepinephrine to higher temperatures.

Therefore, there is a need for improved stable, low concentration, ready-to-inject and antioxidant free norepinephrine formulations, and methods of manufacturing and storing the same.

SUMMARY OF THE INVENTION

The inventive subject matter is directed to antioxidant free sterilizable/autoclavable ready-to-inject norepinephrine compositions having improved stability and a physiologically acceptable pH.

In one aspect of the inventive subject matter, the inventors contemplate a ready to ready-to-inject norepinephrine composition that comprises an aqueous acidic buffer having a pH range of between 3.7 and 4.3, wherein the aqueous buffer further comprises a chelating agent and a pharmaceutically acceptable salt. Most typically, the chelating agent is present in an amount of between 1 µg/ml and 100 µg/ml, and the pharmaceutically acceptable salt is present in an amount of between 0.6 wt % and 1.2 wt %. Norepinephrine (typically enantiomerically pure (i.e., at least 98%) R-isomer) is dissolved at a concentration that is suitable for administration to a patient in need thereof. In further preferred aspects, the ready-to-administer norepinephrine composition is substantially free of antioxidants, and the ready-to-administer norepinephrine composition is formulated such that after storage over at least three months equal or less than 10% of the R-isomer form will isomerize to the S-isomer and such that equal or less than 5% of the total norepinephrine will degrade to degradation products. As used herein, reference to the term norepinephrine should be interpreted broadly to include pharmaceutically acceptable salts and prodrugs thereof.

Therefore, the inventors also contemplate a method of preparing a ready-to-inject norepinephrine composition that includes a step of formulating a liquid parenteral composition that contains in an aqueous acidic buffer norepinephrine as an R-isomer such that (a) the formulation exhibits less than 10% of isomerization of the R-isomer to an S-isomer after three months of storage of the liquid composition, and (b) the formulation exhibits equal or less than 5% degradation of total norepinephrine after three months of storage of the liquid composition. The aqueous acidic buffer will typically have a pH range of between 3.7 and 4.3, and the aqueous buffer will further comprise a chelating agent and a pharmaceutically acceptable salt. In such methods, the total norepinephrine is present in the liquid parenteral composition at a concentration of between 10 µg/ml and 100 µg/ml, and the ready-to-inject norepinephrine composition is substantially free of antioxidants.

Viewed form a different perspective, the inventors also contemplate a method of preparing a ready-to-inject norepinephrine composition that includes the steps of preparing an aqueous acidic buffer at a pH range of between 3.7 and 4.3, wherein the aqueous buffer also includes a chelating agent and a pharmaceutically acceptable salt. Preferably, the chelating agent is present in an amount of between 1 µg/ml and 100 µg/ml, and tonicity is adjusted with the pharmaceutically acceptable salt (e.g., NaCl). In a further step, norepinephrine (preferably enantiomerically pure R-isomer) is dissolved at a concentration suitable for administration to a patient in need thereof, and the ready-to-administer norepinephrine composition is formulated such that after storage over at least three months equal or less than 10% of the R-isomer form will isomerize to the S-isomer and such that equal or less than 5% of the total norepinephrine will degrade to degradation products. As before, it is generally preferred that the ready-to-administer norepinephrine composition is substantially free of antioxidants. In yet another step, the composition is autoclaved to sterility.

Most typically, but not necessarily, the aqueous acidic buffer is a citrate buffer and/or preferably has a concentration of between 5 mM and 20 mM. Furthermore, preferred aqueous acidic buffers will have a pH of between 3.8 and 4.2. With respect to the chelating agent it is contemplated that such agents are a bicarboxylic acid (e.g., optionally hydroxylated, tartrate), a tricarboxylic acid (e.g., aconitic acid, trimesic acid, citric acid), and/or an aminopolycarboxylic acid (e.g., EDTA, EGTA, etc.), and that such chelating agents are present at low concentrations, preferably between 1 µg/ml and 10 µg/ml, or between 10 µg/ml and 100 µg/ml. The norepinephrine is typically present at a concentration of between 10 µg/ml and 100 µg/ml, for example, at a concentration of 16 µg/ml (+/−10%), 32 µg/ml (+/−10%), or 64 µg/ml (+/−10%). Contemplated methods may also include a step of autoclaving the compositions.

With respect to stability it is contemplated that the storage condition is over at least three months at 40° C. and 75% (+/−5) relative humidity, that equal or less than 6% of the R-isomer form will isomerize to the S-isomer, and/or that equal or less than 3.5% of the total norepinephrine will degrade to degradation products.

Where desired, contemplated compositions have a dissolved oxygen concentration of equal or less than 1 ppm (e.g., by formulating the liquid parenteral composition using deoxygenated water), and/or or by packaging the composition together with a (preferably metal free) oxygen scavenger. Packaging may further make use of a container that is configured (e.g., aluminized or otherwise treated) to reduce light-mediated oxidation of the norepinephrine.

DETAILED DESCRIPTION OF THE INVENTION

The inventive subject matter is directed to stable aqueous pharmaceutical preparations of norepinephrine (and pharmaceutically acceptable salts thereof) in a ready-to-inject form that are sterile and preferably substantially free of antioxidants. Most preferably, stability of such compositions is characterized by low (oxidative and photo-induced) degradation as well as low isomerization.

More specifically, the inventors have discovered that formulations can be prepared that will exhibit less than 8%, more typically less than 6%, even more typically less than 4%, and most typically less than 3% of degradation as determined by HPLC-UV, and that will exhibit less than 10%, more typically less than 8%, even more typically less than 6%, and most typically less than 4% of isomerization from R- to S-configuration as determined by HPLC-UV. Most notably, such formulations were found to be stable over extended periods without antioxidants (e.g., at least 1 month, or at least two months, or at least three months), even at elevated storage temperatures (e.g., accelerated storage conditions such as 40° C. and 75% relative humidity (+/−5%)). Even more remarkable, such formulations could also be subjected to thermal sterilization, and particularly sterilizing to sterility (e.g., over at least 5 min, or at least 10 min, or at least 15 min at 121° C.), without substantial increase (i.e., >1.5%, or >1.0%, or >0.7%) of the S-isomer of norepinephrine.

Additionally, it should be appreciated that contemplated formulations can be filled in a polymer bag (e.g., polypropylene) or other container that may subsequently be placed into a secondary container together with an oxygen scavenger, and especially a metal-free oxygen scavenger. Most typically, at least one of the polymer bag and the secondary container may be impervious to light in general or light of a wavelength that promotes photo-initiated degradation. For example, containers may be metalized (e.g., aluminized) or combined or coated with carbonaceous materials or other dye(s). If desired, contemplated formulations are sufficiently stable to also allow filling into containers using a blow-fill-seal (BFS) process.

Therefore, contemplated norepinephrine formulations of the inventive subject matter can advantageously be provided in a ready-to-inject form to thereby avoid the inconvenience associated with diluting concentrated small volume norepinephrine parenteral formulations into diluents prior to infusion. Thus, the ready-to-inject formulations also eliminate microbial contamination risks and calculation errors associated with dilution. Most typically, contemplated formulations will be available in a range of concentrations commonly required by medical practitioners for emergency restoration of blood pressure, for example in cases of acute hypotension. Consequently, norepinephrine will typically be present in formulations at a concentration of between 10 µg/ml and 100 µg/ml, including concentration of 16 µg/ml (+/−10%), 32 µg/ml (+/−10%), and 64 µg/ml (+/−10%).

As will be readily appreciated, the norepinephrine for preparation of contemplated formulations is preferably (R)-Norepinephrine, or enantiomerically pure (i.e., at least 98% R-isomer) norepinephrine. However, in less preferred aspects, isomeric purity can also be between 95-98%, or even between 90-95%. Of course, it should also be appreciated that the norepinephrine may be a salt of any suitable and pharmaceutically acceptable form, including mineral salts (e.g., HCl salt) and organic salts (e.g., bitartrate). Similarly, where desired, the norepinephrine may also be used in any suitable prodrug form (e.g., β,3-dihydroxytyrosine, L-dihydroxyphenylserine, etc.).

Suitable buffers are generally buffers that stabilize the pH of the contemplated liquid formulations in an acidic pH range and will therefore include glycine buffers, citrate buffers, citrate/phosphate buffers, acetate buffers, etc. However, the inventors have further discovered that where the norepinephrine is provided as the norepinephrine bitartrate salt, a buffer can advantageously be omitted and the pH can be adjusted with suitable acid and/or base as is well known in the art. Notably, the bitartrate appeared to act as a weak buffer in the stability range for the norepinephrine as is shown in more detail below. Most typically the pH of the formulation will be less than 5.0 and more typically less than 4.5, and most typically less than 4.3, but higher than 3.0, more typically higher than 3.5, and most typically higher than 3.7. For example, suitable buffers will have a pH in the range of between 3.7 and 4.3, or between 3.7 and 4.0, or between 3.8 and 4.1, or between 3.9 and 4.2, or between 4.0 and 4.2. Notably, such pH range provided remarkable stability for low concentrations of norepinephrine, especially when in combination with a chelator and a salt. While not limiting to the inventive subject matter, the buffer strength is typically relatively low, for example, equal or less than 100 mM, and more typically equal or less than 50 mM, and most typically between 5 mM and 20 mM (e.g., 10 mM).

Moreover, in further contemplated aspects, the formulation will also include one or more chelating agents, and particularly metal ion chelators. For example, suitable chelators include various bicarboxylic acids, tricarboxylic acids, and aminopolycarboxylic acids such as ethylenediaminetetraacetic acid (EDTA), ethylene glycol-bis(β-aminoethyl ether)-N,N,N',N'-tetraacetic acid (EGTA), and penta(carboxymethyl)diethylenetriamine (DTPA), and salts and hydrates thereof. While not limiting to the inventive subject matter, it is contemplated that the metal ion chelators will slow down both the baseline and metal ion-stimulated autoxidation of norepinephrine. Remarkably, the inventors unexpectedly observed that the desirable effect of the chelators was observable at relatively low concentrations of the chelators. For example, reduction of the baseline and metal ion-stimulated autoxidation of norepinephrine was observed at chelator concentrations of between 1 µg/ml and 10 µg/ml, and between 10 µg/ml and 100 µg/ml. Interestingly, the chelators, and especially the aminopolycarboxylic acids retained stabilizing effect despite the relatively low pH favoring protonated forms of the chelators.

With respect to suitable salts it is contemplated that the salt is a pharmaceutically acceptable salt that can be used to increase tonicity. Therefore, pharmaceutically acceptable salts are contemplated, and especially NaCl, at a concentration of at least 0.6 wt %, or at least 0.7 wt %, or at least 0.8 wt %, or at least 0.9 wt %. For example, suitable salt concentrations are between 0.6 wt % and 1.2 wt %. Depending on the particular salt concentration, additional tonicity agents may be added and suitable tonicity agents include glycerol, thioglycerol, mannitol, lactose, and dextrose. The amount of tonicity adjusting agent used can be adjusted to obtain osmolality of the formulations in the range of 260 to 340 mOsm/kg. An osmometer can be used to check and adjust the amount of tonicity adjusting agent to be added to obtain the desired osmolality.

It should further be appreciated that contemplated compositions are substantially free of antioxidants (i.e., do not include antioxidants in an amount effective to reduce degradation of total norepinephrine by at least 1% when stored over a period of at least three months at 25° C. Indeed, the inventors unexpectedly discovered that some formulations with antioxidants (particularly with ascorbic acid) had decreased stability. Notably, contemplated formulations were stable as described in more detail below, even in the absence of effective quantities of antioxidants, especially where deoxygenated solvents (e.g., typically water and/or buffer) were employed. Deoxygenation (i.e., reduction of molecular dissolved oxygen) can be achieved in numerous manners, including sparging with inert gases (e.g., helium, various freons, argon, xenon), agitation under vacuum, and/or using enzymatic systems that deplete a solution of dissolved oxygen (see e.g., U.S. Pat. No. 9,187,779). Additionally, or alternatively, ingress of molecular oxygen into the formulation can also be reduced by co-packaging a container with the formulation in a secondary container that includes an oxygen scavenger, and especially a metal-free oxygen scavenger (e.g., GLS100, Ageless®, Pharmakeep®, all commercially available from Mitsubishi Gas Chemical America).

With respect to the sterilization of contemplated formulations it should be appreciated that contemplated formulations may be sterilized using all known manners of sterilization, including filtration through 0.22 micron filters, heat sterilization, autoclaving, radiation (e.g., gamma, electron beam, microwave). Unexpectedly, and as shown in more detail below, the inventors have also discovered that contemplated formulations were heat stable and did not undergo significant isomerization, even under conditions of sterilization (exposure to high-pressure saturated steam) at 121° C. for at least 5, or at least 10, or at least 15 minutes.

Based on the unexpected heat stability, the formulations contemplated herein can also be filtered through a 0.22 micron filter, and filled in to a polyethylene, polypropylene or low-density polyethylene containers in a blow-fill-seal (BFS) process. BFS is a form of advanced aseptic manufacturing wherein the container is formed, filled, and sealed in one continuous, automated system not requiring human intervention. The process begins with the extrusion of plastic granules in the form of a hot hollow pipe of molten plastic called a parison. The next step is the blow molding of the container with an open top through which the container is filled, all while the plastic remains hot and in a molten state. Once filled, the container is hermetically sealed and cooled. The blow-fill seal process can take several seconds, and contemplated ready-to-inject compositions advantageously are formulated to withstand the temperature and pressure requirements without substantial degradation of norepinephrine (e.g., less than 5 wt %, less than 3 wt %, less than 2 wt %, less than 1 wt % degradation).

Once the norepinephrine formulations are filled in large volume polymeric, semi-permeable infusion containers (e.g., BFS container or flexible IV bags), the containers can optionally be layered or covered with a secondary packaging system including an aluminum pouch or other oxygen scavenger. For example, the BFS containers can further be sealed in an oxygen and moisture barrier blister packaging. The blister packaging can comprise one or more layers, and the one or more layers can include aluminum foil or other oxygen absorber having an Oxygen Transmission Rate (OTR) between 0.0005 to 5.00 cc/100 $in^2$/24 hrs. Additionally or alternatively, one or more oxygen absorbers (metal or metal free, organic material) can be incorporated into any portion of the BFS container, the secondary packaging system, or between the two (e.g., between the BFS container and the multi-layer packaging) such that the oxygen absorber removes at least a portion of oxygen from the air surrounding said oxygen-sensitive drug. A beneficial feature of the oxygen absorber is the absorbance and removal of oxygen present in the primary packaging and in the liquid drug itself. Notably, it was found that the oxygen absorber also removed residual headspace oxygen in the primary packaging and also dissolved oxygen in the liquid over time, thereby further improving stability of norepinephrine.

The following examples are provided for illustrative purposes only and should not be interpreted as limiting the present invention.

EXAMPLES

The following examples illustrate some of the experiments leading to the formulations according to the inventive subject matter, however, should not be construed to limit the scope of the claims in any way.

Stability and Isomerization: The ionization behavior of norepinephrine in aqueous solution is complex. Common with other o-hydroquinone systems, norepinephrine in aqueous solution is susceptible to oxidation to form the corresponding o-quinone, which can then also undergo various secondary reactions, which also becomes more prevalent as the pH becomes more alkaline. Norepinephrine may further isomerize to the pharmacologically less active S-enantiomer at low pH values, corresponding to protonation of the hydroxyl group at the benzylic chiral center. Therefore, to prevent norepinephrine cyclization reactions pH values less than 6.0 are desired. A pH range of 3.0 to 6.2 was screened to determine pH of optimum stability. Composition of norepinephrine bitartrate equivalent to 16 µg/mL norepinephrine base at various pH values were prepared are described below, with Table 4 listing compositions of norepinephrine bitartrate in citrate buffer (10 mM), For preparation of the solutions, about 90% of the final quantity of water was collected in a glass media bottle. Nitrogen ($N_2$) gas was purged for about thirty minutes to reduce the dissolved oxygen levels. Sodium chloride was added and the solution was stirred until a homogenous solution was obtained. Citric acid was added and the solution was stirred until a homogenous solution was obtained. The pH of the bulk solutions was adjusted to pH 3.0, 3.4, 3.8, 4.2, 4.6, 5.0, 5.4, 5.8, and 6.2, respectively for each formulation composition using sufficient quantity of 10% w/v sodium hydroxide or 10% w/v hydrochloric acid. Norepinephrine bitartrate was added and the solution was stirred for approximately 10 minutes until a clear solution was formed. Solutions were made up to volume with water. The solutions were filled into 10 mL glass vials, overlaid with nitrogen, stoppered, and sealed. The stability was studied at 4° C., 25° C., and 60° C. by assay. Samples were observed visually for precipitation and change in color for a period of 7 days. Data are presented in Table 5.

No change in physical appearance was observed in the solutions stored at 4° C. In the solutions stored at 25° C., a change in color was observed at pH 6.2. Red brown color was observed in solutions stored at or above pH 5.0 at 60° C. Oxidation and color formation are very common with norepinephrine in unfavorable conditions and the speed of the reaction and the nature of the final products are dependent on the catalysts (e.g., metal ion impurities) and buffers employed. A pH range from 3.0 to 4.5 was selected for further testing.

Stability of Norepinephrine in selected pH ranges and formulations: The formulations for the next experiments are shown in Table 6 below, involving three different compositions of norepinephrine bitartrate at three different pH (3.5, 4.0, 4.5, and 5.0) values. Lab scale batches were prepared and subjected to lab scale stability tests at accelerated (40° C./75% RH) and long term stability (25° C./60% RH) storage conditions. The test results from the stability studies are presented in Table 7-Table 10, with CCS indicating Clear colorless solution; ND indicating Not Detected; NR indicating Not Reported (<0.05%); and NT indicating Not Tested.

TABLE 4

Compositions of Norepinephrine Bitartrate for pH dependent stability in Citrate Buffer (10 mM).

| Ingredients | Concentration (mg/mL) | | | | | | | | |
|---|---|---|---|---|---|---|---|---|---|
| | I | II | III | IV | V | VI | VII | VIII | IX |
| Norepinephrine Bitartarate equivalent to Norepinephrine base | 0.016 | 0.016 | 0.016 | 0.016 | 0.016 | 0.016 | 0.016 | 0.016 | 0.016 |
| Sodium Chloride | 9 | 9 | 9 | 9 | 9 | 9 | 9 | 9 | 9 |
| Citric acid | 1.92 | 1.92 | 1.92 | 1.92 | 1.92 | 1.92 | 1.92 | 1.92 | 1.92 |
| Sodium Citrate | 2.94 | 2.94 | 2.94 | 2.94 | 2.94 | 2.94 | 2.94 | 2.94 | 2.94 |
| HCl/NaOH (q.s. pH) | 3.0 | 3.4 | 3.8 | 4.2 | 4.6 | 5.0 | 5.4 | 5.8 | 6.2 |
| Water for Injection (q.s. mL) | 1 | 1 | 1 | 1 | 1 | 1 | 1 | 1 | 1 |

TABLE 5

Effect of pH on stability of Norepinephrine Bitartrate in citrate buffer.

| Temperature | Formulation | Assay $T_0$ | Assay $T_7$ | pH | Color | Precipitation |
|---|---|---|---|---|---|---|
| 4° C. | I | 96.4 | 96.5 | 3.0 | No | No |
| | II | 98.0 | 97.5 | 3.4 | No | No |
| | III | 99.0 | 98.5 | 3.8 | No | No |
| | IV | 99.1 | 98.4 | 4.2 | No | No |
| | V | 98.1 | 98.6 | 4.6 | No | No |
| | VI | 98.4 | 98.1 | 5.0 | No | No |
| | VII | 97.1 | 96.6 | 5.4 | No | No |
| | VIII | 97.8 | 97.5 | 5.8 | No | No |
| | IX | 91.5 | 91.2 | 6.2 | No | No |
| 25° C. | I | 96.4 | 96.4 | 3.0 | No | No |
| | II | 98.0 | 97.5 | 3.4 | No | No |
| | III | 99.0 | 97.9 | 3.8 | No | No |
| | IV | 99.1 | 97.7 | 4.2 | No | No |
| | V | 98.1 | 97.3 | 4.6 | No | No |
| | VI | 98.4 | 97.3 | 5.0 | No | No |
| | VII | 97.1 | 95.9 | 5.4 | No | No |
| | VIII | 97.8 | 94.5 | 5.8 | No | No |
| | IX | 91.5 | 80.4 | 6.2 | Yes | No |
| 60° C. | I | 96.4 | 95.2 | 3.0 | No | No |
| | II | 98.0 | 95.0 | 3.4 | No | No |
| | III | 99.0 | 95.2 | 3.8 | No | No |
| | IV | 99.1 | 93.2 | 4.2 | No | No |
| | V | 98.1 | 88.9 | 4.6 | No | No |
| | VI | 98.4 | 77.4 | 5.0 | Yes | No |
| | VII | 97.1 | 46.8 | 5.4 | Yes | No |
| | VIII | 97.8 | NT | 5.8 | Yes | No |
| | IX | 91.5 | NT | 6.2 | Yes | No |

TABLE 6

Formulation composition selected for further development activities and optimization

| | Quantity (mg/mL) | | | |
|---|---|---|---|---|
| | Formulation | | | |
| Ingredient | X | XI | XII | XIII |
| Norepinephrine Bitartrate | 0.016 | 0.016 | 0.016 | 0.016 |
| Edetate Sodium | 0.10 | 0.10 | 0.10 | 0.10 |
| Sodium chloride | 9 | 9 | 9 | 9 |
| HCl/NaOH | q.s. pH 3.5 | q.s. pH 4.0 | q.s. pH 4.5 | q.s. pH 5.0 |
| Water for Injection Q.S. | 1 ml | 1 ml | 1 ml | 1 ml |
| Dissolved Oxygen (ppm) | <1 | <1 | <1 | <1 |

TABLE 7

Stability study of Formulation X - Norepinephrine Bitartrate Injection (16 μg/ml) filled in glass vial (pH 3.5).

| | Storage Condition | | | | | | | | | | | | |
|---|---|---|---|---|---|---|---|---|---|---|---|---|---|
| | 25 ± 2° C./60 ± 5% RH | | | | | | | 40 ± 2° C./75 ± 5% RH | | | | | |
| | Time Point | | | | | | | | | | | | |
| | Initial | 1 Month | 2 Month | 3 Month | 4 Month | 5 Month | 6 Month | 1 Month | 2 Month | 3 Month | 4 Month | 5 Month | 6 Month |
| Appearance | CCS | CCS | CCS | CCS | CCS | CCS | CCS | CCS | CCS | CCS | CCS | CCS | CCS |
| pH | 3.50 | 3.65 | 3.59 | 3.56 | 3.58 | 3.54 | 3.48 | 3.66 | 3.61 | 3.59 | 3.64 | 3.60 | 3.59 |
| Assay | 101.4 | 99.6 | 97.1 | 97.1 | 101.0 | 102.3 | 102.2 | 99.5 | 97.0 | 98.7 | 100.4 | 101.7 | 101.4 |
| S-form | NT | NT | NT | NT | 1.8 | 2.2 | 2.2 | NT | NT | NT | 7.6 | 8.1 | 9.8 |
| Total | ND | ND | ND | ND | ND | ND | ND | ND | ND | ND | ND | ND | ND |

TABLE 8

Stability study of Formulation XI - Norepinephrine Bitartrate Injection (16 μg/ml) filled in glass vial (pH 4.0).

| | Storage Condition | | | | | | | | |
|---|---|---|---|---|---|---|---|---|---|
| | 25 ± 2° C./60 ± 5% RH | | | | | 40 ± 2° C./75 ± 5% RH | | | |
| | Time Point | | | | | | | | |
| | Initial | 1 Month | 2 Month | 3 Month | 6 Month | 1 Month | 2 Month | 3 Month | 6 Month |
| Appearance | CCS | CCS | CCS | CCS | CCS | CCS | CCS | CCS | CCS |
| pH | 4.02 | 3.96 | 3.98 | 3.97 | 3.91 | 4.01 | 3.99 | 4.02 | 4.03 |
| Assay | 101.3 | 98.7 | 95.5 | 99.2 | 100.5 | 98.6 | 95.3 | 97.1 | 97.5 |
| S-form | NT | NT | NT | NT | 1.7 | NT | NT | NT | 7.8 |
| Total Impurities | 0.1 | ND | 0.06 | ND | 0.80 | ND | 0.06 | 0.1 | 0.79 |

TABLE 9

Stability study of Formulation XII - Norepinephrine Bitartrate Injection (16 μg/ml) filled in glass vial (pH 4.5).

| | Storage Condition | | | | | | | | |
|---|---|---|---|---|---|---|---|---|---|
| | 25 ± 2° C./60 ± 5% RH | | | | | 40 ± 2° C./75 ± 5% RH | | | |
| | Time Point | | | | | | | | |
| | Initial | 1 Month | 2 Month | 3 Month | 6 Month | 1 Month | 2 Month | 3 Month | 6 Month |
| Appearance | CCS | CCS | CCS | CCS | CCS | CCS | CCS | CCS | CCS |
| pH | 4.50 | 4.35 | 4.36 | 4.32 | 4.33 | 4.33 | 4.40 | 4.39 | 4.29 |
| Assay | 100.1 | 98.9 | 95.5 | 98.2 | 97.9 | 97.1 | 92.5 | 93.7 | 77.2 |
| S-form | NT | NT | NT | NT | 1.2 | NT | NT | NT | 2.9 |
| Total Impurities | ND | 0.32 | 0.79 | 0.52 | 3.41 | 1.18 | 0.38 | 5.59 | 10.38 |

TABLE 10

Stability study of Formulation XIII - Norepinephrine Bitartrate Injection (16 μg/ml) filled in glass vial (pH 5.0).

| | Storage Condition | | | | | | | | |
|---|---|---|---|---|---|---|---|---|---|
| | 25 ± 2° C./60 ± 5% RH | | | | | 40 ± 2° C./75 ± 5% RH | | | |
| | Time Point | | | | | | | | |
| | Initial | 1 Month | 2 Month | 3 Month | 4 Month | 1 Month | 2 Month | 3 Month | 4 Month |
| Appearance | CCS | CCS | CCS | CCS | CCS | CCS | CCS | CCS | CCS |
| pH | 4.99 | 4.62 | 4.51 | 4.57 | 4.51 | 4.87 | 4.81 | 4.83 | 4.53 |
| Assay | 102.7 | 100.5 | 95.6 | 99.2 | 100.4 | 98.3 | 89.8 | 87.0 | 72.3 |
| S-form | NT | NT | NT | NT | 1.2 | NT | NT | NT | 3.0 |
| Total Impurities | ND | 0.75 | 0.81 | 0.48 | 1.29 | 0.94 | 2.4 | 5.39 | 14.91 |

Based on the above considerations, the effect of different levels of EDTA on stability of norepinephrine was determined. Three batches at concentrations of 16 µg/mL, 32 µg/mL, and 64 µg/mL were made with EDTA concentrations of 100 µg/mL: Formulation XIV (16 µg/mL), Formulation XV (32 µg/mL), Formulation XVI (64 µg/mL). Two additional batches were made at 10 µg/mL EDTA Formulation XVII and 1 µg/mL EDTA (Formulation XVIII) at 64 µg/mL Norepinephrine. The composition of the batches is specified in Table 11. The drug product was compounded as described earlier and packaged in 250 mL in polypropylene bags. This was further packed into aluminum overwrap with an oxygen scavenger (GLS 100, Mitsubishi Gas Chemicals). The batches were then stored at room temperature and accelerated temperature conditions.

TABLE 11

Formulation composition selected with different level of EDTA concentrations.

| | Quantity (mg/mL) Formulation Number | | | | |
|---|---|---|---|---|---|
| Ingredient | XIV | XV | XVI | XVII | XVIII |
| Norepinephrine Bitartrate | 0.016 | 0.032 | 0.064 | 0.064 | 0.064 |
| Edetate Sodium | 0.10 | 0.10 | 0.10 | 0.010 | 0.0010 |
| Sodium chloride | 9 | 9 | 9 | 9 | 9 |
| Hydrochloric Acid/ Sodium Hydroxide | q.s. pH 4.0 | q.s. pH 4.0 | q.s. pH 4.0 | q.s. pH 4.0 | q.s. pH 4.0 |
| Water for Injection | q.s. 1 ml | q.s. 1 ml | q.s. 1 ml | q.s. 1 ml | q.s. 1 ml |

The resultant stability data on these formulations are presented in Table 12-Table 16 (CCS—Clear colorless solution; ND—Not Detected). The results of the stability studies at different amounts of EDTA at pH 4.0 indicates that both 0.01%, 0.001% of EDTA significantly prevented the degradation rate of norepinephrine in terms of known and unknown impurities. Moreover, with respect to isomerization from the R-isomer to the S-isomer it was notably observed that the amount of EDTA had substantially no influence on racemization or enantiomer formation during stability and after autoclaving.

TABLE 12

Stability study of Formulation XIV - Norepinephrine bitartrate injection (16 µg/mL); pH 4.0 at 100 µg/mL EDTA.

| | Storage Condition | | | | | | |
|---|---|---|---|---|---|---|---|
| | 25 ± 2° C./60 ± 5% RH | | | | 40 ± 2° C./75 ± 5% RH | | |
| | Time Point | | | | | | |
| | Initial | 1 Month | 2 Month | 3 Month | 1 Month | 2 Month | 3 Month |
| Appearance | CCS | CCS | CCS | CCS | CCS | CCS | CCS |
| pH | 3.99 | 3.96 | 4.08 | 4.08 | 4.02 | 4.08 | 4.08 |
| Assay | 98.5 | 100.4 | 100.1 | 99.7 | 100.3 | 100.0 | 99.5 |
| S-form | 0.9 | 1.1 | 1.4 | 1.3 | 1.9 | 2.9 | 4.2 |
| Total Impurities | 0.05 | ND | ND | ND | ND | 0.10 | 0.38 |

TABLE 13

Stability study of Formulation XV - Norepinephrine bitartrate injection (32 µg/mL); pH 4.0 at 100 µg/mL EDTA.

| | Storage Condition | | | | | | |
|---|---|---|---|---|---|---|---|
| | 25 ± 2° C./60 ± 5% RH | | | | 40 ± 2° C./75 ± 5% RH | | |
| | Time Point | | | | | | |
| | Initial | 1 Month | 2 Month | 3 Month | 1 Month | 2 Month | 3 Month |
| Appearance | CCS | CCS | CCS | CCS | CCS | CCS | CCS |
| pH | 4.01 | 3.99 | 4.08 | 4..08 | 4.02 | 4.08 | 4.08 |
| Assay | 101.0 | 102.9 | 97.1 | 100.7 | 102.9 | 99.4 | 100.6 |
| S-form | 0.9 | 1.1 | 1.3 | 1.4 | 1.9 | 3.0 | 4.1 |
| Total Impurities | 0.06 | ND | ND | ND | ND | ND | 0.14 |

TABLE 14

Stability study of Formulation XVI - Norepinephrine bitartrate injection (64 μg/mL); pH 4.0 at 100 μg/mL EDTA.

| | Storage Condition | | | | | | |
|---|---|---|---|---|---|---|---|
| | 25 ± 2° C./60 ± 5% RH | | | | 40 ± 2° C./75 ± 5% RH | | |
| | Time Point | | | | | | |
| | Initial | 1 Month | 2 Month | 3 Month | 1 Month | 2 Month | 3 Month |
| Appearance | CCS | CCS | CCS | CCS | CCS | CCS | CCS |
| pH | 4.00 | 3.99 | 4.08 | 4.08 | 3.98 | 4.07 | 4.07 |
| Assay | 98.4 | 103.2 | 98.7 | 100.2 | 104.6 | 99.3 | 99.8 |
| S-form | 0.9 | 1.1 | 1.3 | 1.3 | 2.0 | 3.2 | 4.2 |
| Total Impurities | 0.06 | ND | 0.12 | ND | ND | ND | ND |

TABLE 15

Stability study of Formulation XVII - Norepinephrine bitartrate injection (64 μg/mL); pH 4.0 at 10 μg/mL EDTA.

| | Storage Condition | | | | | | |
|---|---|---|---|---|---|---|---|
| | 25 ± 2° C./60 ± 5% RH | | | | 40 ± 2° C./75 ± 5% RH | | |
| | Time Point | | | | | | |
| | Initial | 1 Month | 2 Month | 3 Month | 1 Month | 2 Month | 3 Month |
| Appearance | CCS | CCS | CCS | CCS | CCS | CCS | CCS |
| pH | 4.00 | 3.98 | 4.06 | 4.06 | 3.99 | 4.05 | 4.05 |
| Assay | 102.7 | 105.7 | 103.4 | 104.3 | 107.8 | 103.6 | 103.9 |
| S-form | 0.9 | 1.1 | 1.2 | 1.5 | 2.0 | 3.3 | 4.3 |
| Total | 0.06 | ND | ND | ND | ND | 0.26 | ND |

TABLE 16

Stability study of Formulation XVIII - Norepinephrine bitartrate injection (64 μg/mL); pH 4.0 at 1 μg/mL EDTA.

| | Storage Condition | | | | | | |
|---|---|---|---|---|---|---|---|
| | 25 ± 2° C./60 ± 5% RH | | | | 40 ± 2° C./75 ± 5% RH | | |
| | Time Point | | | | | | |
| | Initial | 1 Month | 2 Month | 3 Month | 1 Month | 2 Month | 3 Month |
| Appearance | CCS | CCS | CCS | CCS | CCS | CCS | CCS |
| pH | 4.00 | 3.98 | 4.07 | 4.07 | 4.02 | 4.06 | 4.06 |
| Assay | 98.7 | 102.6 | 100.4 | 100.4 | 105.0 | 99.9 | 99.2 |
| S-form | 0.9 | 1.1 | 1.3 | 1.4 | 2.0 | 3.2 | 4.3 |
| Total | 0.06 | ND | ND | ND | ND | ND | ND |

Sterilization and Stability: The volume for ready-to-inject formulations is 250 mL and as such classifies as a large volume parenteral (LVP). To achieve a desired or required sterility assurance level of $10^{-6}$ for a LVP terminal sterilization via heat it is typically required. The inventors therefore investigated whether or not contemplated formulations could be terminally sterilized via autoclaving.

Formulations at a concentration 16 μg/mL and 64 μg/mL (Formulation XVII) Norepinephrine base were prepared substantially as shown in Table 11 above and packaged in secondary packaging of aluminum overwrap with an oxygen scavenger and shipped for terminal sterilization. The secondary packaging was removed and the bags were terminally sterilized using steam sterilizer (Fedegari, Model # FOB3) with an air over-pressure (AOP) sterilization cycle. The terminal sterilization was performed at 121° C. for 5, 10, and 15 min. Post completion of sterilization temperature, the bags underwent spontaneous cooling to 95° C. and forced cooling to 70° C. The total exposure time and calculated $F_0$ values were 11.09, 17.04, and 22.42 for 5 min, 10 min, and 15 min cycles respectively. The bags were then analyzed for assay, impurities, and S-isoform, and the results are shown in Table 17 and Table 18.

TABLE 17

Stability study of Norepinephrine bitartrate injection (16 μg/mL) filled in 100 mL PP bags (pH 4.0); 10 μg/mL EDTA; terminally sterilized.

| | Time Point | | | | | | | | | |
|---|---|---|---|---|---|---|---|---|---|---|
| | Initial | 5 Min | | | 10 Min | | | 15 Min | | |
| | | Bag Number | | | | | | | | |
| | | 1 | 2 | 3 | 1 | 2 | 3 | 1 | 2 | 3 |
| Appearance | CCS | CCS | CCS | CCS | CCS | CCS | CCS | CCS | CCS | CCS |
| pH | 3.76 | 3.85 | 3.78 | 3.77 | 3.76 | 3.76 | 3.78 | 3.76 | 3.75 | 3.76 |
| Dissolved Oxygen | 0.63 | 4.93 | 4.86 | 4.89 | 0.75 | 0.48 | 0.55 | 0.65 | 0.78 | 0.77 |
| Assay | 103.1 | 103.1 | 103.1 | 103.1 | 103.1 | 103.0 | 103.1 | 103.1 | 103.2 | 103.1 |
| S-Form | 1.0 | 3.0 | 3.0 | 3.0 | 3.8 | 3.7 | 3.7 | 4.3 | 4.3 | 4.3 |
| Total | ND | ND | ND | ND | ND | ND | ND | ND | ND | ND |

TABLE 18

Stability study of Norepinephrine bitartrate injection (64 μg/ml) filled in 100 mL PP bags (pH 4.0); 10 μg/mL EDTA terminally sterilized.

| | Time Point | | | | | | | | | |
|---|---|---|---|---|---|---|---|---|---|---|
| | Initial | 5 Min | | | 10 Min | | | 15 Min | | |
| | | Bag Number | | | | | | | | |
| | | 1 | 2 | 3 | 1 | 2 | 3 | 1 | 2 | 3 |
| Appearance | CCS | CCS | CCS | CCS | CCS | CCS | CCS | CCS | CCS | CCS |
| pH | 3.74 | 3.74 | 3.75 | 3.73 | 3.74 | 3.74 | 3.76 | 3.74 | 3.73 | 3.74 |
| Dissolved Oxygen | 0.69 | 5.15 | 5.03 | 5.00 | 0.52 | 0.59 | 0.75 | 0.69 | 0.80 | 0.74 |
| Assay | 101.2 | 102.2 | 101.2 | 101.5 | 101.7 | 101.2 | 101.3 | 101.2 | 101.3 | 102.2 |
| S-Form | 1.0 | 3.0 | 3.0 | 3.0 | 3.7 | 3.7 | 3.7 | 4.3 | 4.3 | 4.3 |
| Total | ND | ND | ND | ND | ND | ND | ND | 0.1 | ND | ND |

As can be seen from the data, the S-isoform appears to increase proportionally to time during the terminal sterilization cycle. No increase in reportable impurities was observed.

Test method—Determination of norepinephrine and degradation products: Separation of Norepinephrine and related compounds was performed using a gradient HPLC method with UV detection. Pentofluorophenylpropyl terminated silica was used as a stationary phase for chromatographic analysis. The mobile phase was prepared by mixing water and methanol, with both solvents containing formic acid. Related compounds were defined by their relative retention times (RRT) based on the NE peak retention time. Quantitation of related compounds was accomplished by comparing the corresponding peak area from a sample solution chromatogram to that of the NE peak from a Reference Standard (RS) solution of a known concentration. Relative Response Factors (RRF) were used to correct for chemical structure effects on the responses of the identified impurities. Chromatography was performed using parameters and methods as shown in Table 19.

TABLE 19

| | |
|---|---|
| HPLC | Waters Alliance e2695 |
| Column | Supelco Discovery HS F-5 Column, 3 μm, 4.6 × 150 mm |
| Column Temperature | 35° C. |
| Sample Temperature | Ambient |
| Injection volume | 85.0 μL |
| Flow Rate | 0.8 mL/min |
| Detection | Spectrum: 200-600 nm, resolution 1.2 nm |

TABLE 19-continued

| | | | |
|---|---|---|---|
| | Single channel: 280 nm, resolution 4.8 nm | | |
| | PDA Filter Time Constant: Normal | | |
| | Sampling rate: 5 points/sec | | |
| Solution A | 0.1% Formic acid in Water | | |
| Solution B | 0.1% Formic acid in Methanol | | |
| | Time (mins) | % Solution A | % Solution B |
| Mobile Phase | 0 | 100 | 0 |
| | 3 | 100 | 0 |
| | 6 | 93 | 7 |
| | 8 | 93 | 7 |
| | 15 | 88 | 12 |
| | 30 | 2 | 98 |
| | 35 | 2 | 98 |
| | 36 | 100 | 0 |
| | 40 | 100 | 0 |

Test Method—Identification, Assay and Enantiomeric Purity of Norepinephrine: Identification and quantification of S-norepinephrine and R-norepinephrine was performed using an HPLC method with UV detection. HPLC-UV was used to separate and quantitate the amount of (R)- and (S)-enantiomers of norepinephrine (NE) present in the drug product with the NE concentrations of 16, 32 and 64 μg/ml. The comparison of the sum of (R)- and (S)-peak responses in a sample chromatogram versus a reference standard chromatogram gives the total amount of NE. The (S)-enantiomer was quantitated based on its peak response as the percentage of the total peak response of both enantiomers.

More specifically, determination of R- and S-enantiomers of norepinephrine in the drug product solution was performed using an isocratic reverse-phase HPLC method with UV detection. Separation was achieved by using a protein-based column with functional chiral selectors. The chiral selector is cellobiohydrolase (CBH), a stable enzyme that has been immobilized onto spherical silica particles. This enzyme preferentially separates compounds containing one or more basic nitrogen groups together with one or more hydrogen-accepting or hydrogen-donating groups. Chromatography was performed using parameters and methods as shown in Table 20.

TABLE 20

| | |
|---|---|
| HPLC | Agilent 1260 Infinity |
| Column | Daicel Chiralpak CBH ™ column, 5 μm, 4.0 × 100 mm |
| Column Temperature | 27° C. ± 2° C. |
| Sample Temperature | Ambient |
| Injection volume | 20.0 μL for 16 mcg/mL, 10.0 μL for 32 mcg/mL, 5.0 μL for 64 mcg/mL |
| Flow Rate | 0.9 mL/min |
| Dection | Single channel: 280 nm, resolution 4.8 nm<br>Spectrum: 200-600 nm, resolution 1.2 nm |
| Mobile phase: | Buffer/IPA 95:5 v/v<br>Buffer: Sodium Phosphate, Disodium Edetate, pH 6.0 |
| Run Time | 8 min |

While contemplated formulations can be administered following various protocols, the inventors contemplate that administration of the formulations, especially administration for treatment of hypotension, will follow a protocol that comprises at least two distinct steps, with an accelerated administration followed by a maintenance administration as exemplarily described in Table 21 below.

TABLE 21

| | | Initial Dose | | Maintenance Dose | |
|---|---|---|---|---|---|
| Presentation (mg/mL) | Concentration (μg/mL) | Dose per Minute (μg/min) | Flow Rate (mL/min) | Dose per Minute (μg/min) | Flow Rate (mL/min) |
| 16 μg/mL (4 mg in 250 mL) | 16 | 8-12 | 0.500-0.750 | 2-4 | 0.125-0.250 |
| 32 μg/mL (8 mg in 250 mL) | 32 | | 0.250-0.375 | | 0.062-0.125 |
| 64 μg/mL (16 mg in 250 mL) | 64 | | 0.125-0.187 | | 0.031-0.062 |

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

It should be apparent, however, to those skilled in the art that many more modifications besides those already described are possible without departing from the inventive concepts herein. The inventive subject matter, therefore, is not to be restricted except in the spirit of the disclosure. One skilled in the art will recognize many methods and materials similar or equivalent to those described herein, which could be used in the practice of the present invention. Indeed, the present invention is in no way limited to the methods and materials described.

Moreover, in interpreting the disclosure all terms should be interpreted in the broadest possible manner consistent with the context. In particular the terms "comprises" and "comprising" should be interpreted as referring to the elements, components, or steps in a non-exclusive manner, indicating that the referenced elements, components, or steps can be present, or utilized, or combined with other elements, components, or steps that are not expressly referenced.

What is claimed is:

1. A ready-to-administer norepinephrine composition, comprising:
   an aqueous solution comprising a chelating agent and a pharmaceutically acceptable salt;
   wherein the chelating agent is an aminopolycarboxylic acid present in an amount of equal or less than 100 μg/ml, and wherein the pharmaceutically acceptable salt is present in an amount of at least 0.7 wt %;
   norepinephrine bitartrate dissolved at a concentration of between 16 and 64 μg/ml, and wherein the norepinephrine is an R-isomer;
   wherein the ready-to-administer norepinephrine composition is substantially free of antioxidants; and
   wherein the ready-to-administer norepinephrine composition is formulated to have a pH range of between 3.8 and 4.2 and has a composition such that after storage over at least three months equal or less than 10% of the R-isomer form will isomerize to the S-isomer and such that equal or less than 5% of the total norepinephrine will degrade to degradation products.

2. The composition of claim 1 wherein the ready-to-administer norepinephrine composition has a pH between 3.8 and 4.1.

3. The composition of claim 1 wherein the ready-to-administer norepinephrine composition has a pH between 3.9 and 4.2.

4. The composition of claim 1 wherein the ready-to-administer norepinephrine composition has a pH of 4.0.

5. The composition of claim 1 wherein the aqueous solution is water.

6. The composition of claim 1 wherein the chelating agent is ethylenediaminetetraacetic acid (EDTA).

7. The composition of claim 1 wherein the chelating agent is present at a concentration of between 10 μg/ml and 100 μg/ml.

8. The composition of claim 1 wherein the chelating agent is 10 μg/ml.

9. The composition of claim 1 wherein the aqueous solution is water, wherein the chelating agent is ethylenediaminetetraacetic acid (EDTA) at a concentration of between 10 μg/ml and 100 μg/ml.

10. The composition of claim 1 wherein the pharmaceutically acceptable salt is present in an amount of 0.9 wt %.

11. The composition of claim 9 wherein the pharmaceutically acceptable salt is present in an amount of 0.9 wt %.

12. The composition of claim 1 wherein the norepinephrine is present at a concentration of about 16 μg/ml, about 32 μg/ml, or about 64 μg/ml.

13. The composition of claim 9 wherein the norepinephrine is present at a concentration of about 16 μg/ml, about 32 μg/ml, or about 64 μg/ml.

14. The composition of claim 11 wherein the norepinephrine is present at a concentration of about 16 μg/ml, about 32 μg/ml, or about 64 μg/ml.

15. The composition of claim 1 wherein the storage over at least three months is at 40° C. and 75% (+/−5%) relative humidity.

16. The composition of claim 1 wherein equal or less than 6% of the R-isomer form will isomerize to the S-isomer.

17. The composition of claim 9 wherein equal or less than 6% of the R-isomer form will isomerize to the S-isomer.

18. The composition of claim 1 wherein equal or less than 3.5% of the total norepinephrine will degrade to degradation products.

19. The composition of claim 1 wherein the composition has a dissolved oxygen concentration of equal or less than 1 ppm.

* * * * *